United States Patent
Sharma

(10) Patent No.: US 7,283,274 B2
(45) Date of Patent: Oct. 16, 2007

(54) METHOD AND SYSTEM FOR PRINTING USER DATA TO FORM DOCUMENTS

(75) Inventor: Manish Sharma, Sunnyvale, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 961 days.

(21) Appl. No.: 09/984,073

(22) Filed: Oct. 26, 2001

(65) Prior Publication Data

US 2003/0081254 A1 May 1, 2003

(51) Int. Cl.
 *G06K 15/00* (2006.01)
(52) U.S. Cl. .................................... 358/1.18; 358/1.1
(58) Field of Classification Search ............... 358/1.18, 358/2.1, 1.11, 1.12, 1.1; 347/129, 151; 345/589, 345/520; 705/2
 See application file for complete search history.

(56) References Cited

U.S. PATENT DOCUMENTS

| | | | | |
|---|---|---|---|---|
| 4,949,392 A * | 8/1990 | Barski et al. | ............... | 382/283 |
| 5,060,980 A * | 10/1991 | Johnson et al. | ............... | 283/70 |
| 5,815,595 A * | 9/1998 | Gugler | ............... | 382/173 |
| 6,559,968 B1 * | 5/2003 | Keronen | ............... | 358/1.18 |
| 6,594,405 B1 * | 7/2003 | Flannery | ............... | 382/302 |
| 6,662,340 B2 * | 12/2003 | Rawat et al. | ............... | 715/507 |
| 6,707,466 B1 * | 3/2004 | Van Sickle et al. | ............... | 345/641 |
| 6,709,176 B2 * | 3/2004 | Gotoh et al. | ............... | 400/61 |
| 6,735,575 B1 * | 5/2004 | Kara | ............... | 705/50 |
| 6,886,136 B1 * | 4/2005 | Zlotnick et al. | ............... | 715/780 |
| 6,898,317 B2 * | 5/2005 | Struble et al. | ............... | 382/209 |
| 2004/0035921 A1 * | 2/2004 | Shioda et al. | ............... | 235/375 |
| 2006/0085222 A1 * | 4/2006 | Huang et al. | ............... | 705/2 |
| 2007/0009158 A1 * | 1/2007 | Geva et al. | ............... | 382/209 |
| 2007/0035755 A1 * | 2/2007 | Maki et al. | ............... | 358/1.9 |

OTHER PUBLICATIONS

Gonzales, R. and Woods, R., Digital Image Processing, Sep. 1993, Addison-Wesley Publishing Company, pp. 31-35.*

* cited by examiner

*Primary Examiner*—Jerome Grant, II

(57) ABSTRACT

A method and apparatus for printing user data to a form document. A scanner scans the form document at low resolution and sends document data to the computer system. User data to be printed on the form document is input into the computer system and displayed as a user data image to be printed onto the form. The scanned document data is used to create a scanned document image. The scanned document image and the user data image are overlaid on the display to indicate to the user how the user data would print onto the hard copy of the scanned document. The scanned document image is aligned with the user data image manually or automatically. The aligned user data image is then printed directly to the scanned document using a printer.

14 Claims, 10 Drawing Sheets

METHOD AND SYSTEM FOR PRINTING USER DATA TO FORM DOCUMENTS

FIELD OF INVENTION

The present invention relates generally to computer and printer systems. More particularly, it relates to systems and methods for printing form documents by scanning the form into a computer system to align user data with the form for printing of the form.

BACKGROUND

In the field of computer printing systems, it is desirable to print user data onto a hard copy of a document, for example to complete blanks on a form document or to add images or handwriting to a user-created document. As used herein, a form or a form document refers to any document to which a user may desire to add user data, and specifically includes without limitation adhesive labels, letterhead and other stationery, user-created documents, and forms such as government forms. User data refers to any information or data that a user desires to add to a form document.

Various systems are known for printing completed forms. The simplest means of completing a form is to use a standard typewriter to manually fill in the blanks of the form. Such a manual system has obvious problems, including the inability to store the user data that is input into the form, the inability to obtain user data from an existing file or similar electronic source, the limitation of user data to alphanumeric keys available on the typewriter, and the generally slow process of completing the form.

Another means of completing forms is to type the user data into a word processor and to print the word processing program data directly onto the form by inserting the form into a manual feed paper tray of the printer. This system requires using a rough estimation of the location of the blanks or other spaces to be completed on the form, for example, by using tabs, spaces, and hard returns. The user might print the user data to a blank sheet of paper and then "eye-ball" the form spaces and the user data, for example by physically overlaying the blank user data and the form document and holding the two up to a light. When the user data is more or less correctly positioned, the user data is printed directly to the form document. This method also has obvious problems, such as problems with accurately aligning the user data with the form and problems spending a significant amount of user time trying to align the two documents.

Another possible means for completing forms would be to create an electronic document from the form document, either by manually entering the form document information or by scanning the form document into a computer system. The electronic form document could be made available in the same format as the user data, for example, in a word processing format. The user can then complete the form by entering the user data into the word processing document. Such a system would also have problems including requiring significant user time to create the electronic form document. Even if the form document is scanned, it still must be formatted into a word processing document. The user may want to ensure that data in existing form documents cannot be changed by the user data, which may require additional formatting time. Also, some forms such as adhesive mailing labels or government documents must be completed on the exact hard copy, rather than on a new sheet of paper. Some form documents may include color coding, symbols, graphics, or similar items that are difficult to scan without capturing a high resolution image and without printing a similarly high resolution image. Obtaining and storing a high resolution image requires significant memory and other resources. This is particularly a problem with portable computer systems, such as laptop or palm-sized computers. In many cases it is more desirable to print user data directly to a form document, rather than creating an entirely new electronic form document.

What is needed is a more efficient way of adding user data to a form document. In particular, what is needed is a more convenient means of printing user data from a computer system directly to a form document using a printer.

SUMMARY OF INVENTION

A method is disclosed for printing user data to a form document, such as letter head, mailing labels, or a more complex form with portions to be completed with user data. The method uses a computer system to align user data with a form document and then prints the user data directly onto the form document. The form document, also referred to as the scanned document, is scanned by a scanner at a low resolution. Scanned document data is sent to a computer system. User data to be printed on the form document is received by the computer system. The user data is displayed as a user data image to be printed onto the form. The scanned document data is used to create a scanned document image. The scanned document image and the user data image are overlaid on the display to indicate to the user how the user data would print onto the hard copy of the scanned document. The scanned document image is aligned with the user data image as desired. The aligned user data image is then printed directly to the scanned document using a printer.

A method is also disclosed for automatically aligning user data with the scanned document image. The method may be performed, for example, by software instructions stored in memory of the computer system, which may be part of a word processing or other application. The scanned document contains user data codes that indicate to the computer system that user data may be required at certain locations on the scanned document. The computer system receives scanned document data including the user data codes. The computer system identifies the user data codes and creates fields for entry of user data based on the codes. Different types of user data codes may be used to indicate different types of user data, which may require different types of fields. The data codes also indicate the position for the fields, relative to the scanned document image generated from the scanned document data. The scanned document image is displayed on a display, including empty fields for entry of user data. The computer system receives user data associated with the fields and displays it in aligned positions determined by the user data codes, as part of a user data image to be printed to the form. When the user data is entered and aligned, the computer system prints the user data image onto the form document using a printer.

A software application including computer-executable instructions stored on a computer-readable medium is also disclosed for aligning user data with a form document, so that the user data may be printed onto a hard copy of the form document. The software application receives scanned document data from a form document scanned at low resolution by a scanner. The application also receives user data to be printed onto the scanned document. The application creates a scanned document image from the scanned document data and a user data image from the user data. The scanned document image and the user data image are displayed on a display in an overlaid manner such that the user can view one document on top of the other. The user data image and/or portions thereof are aligned with the scanned document image as desired. The aligned user data image is then sent to a printer to be printed directly onto the form document. In one embodiment, the scanned document image is used as a background for entering and positioning the user data. In another embodiment, the software instructions recognize user data codes and automatically align user data based on those codes, for example by creating text boxes or other user data boxes at positions determined by the codes.

DETAILED DESCRIPTION

Figure 1:
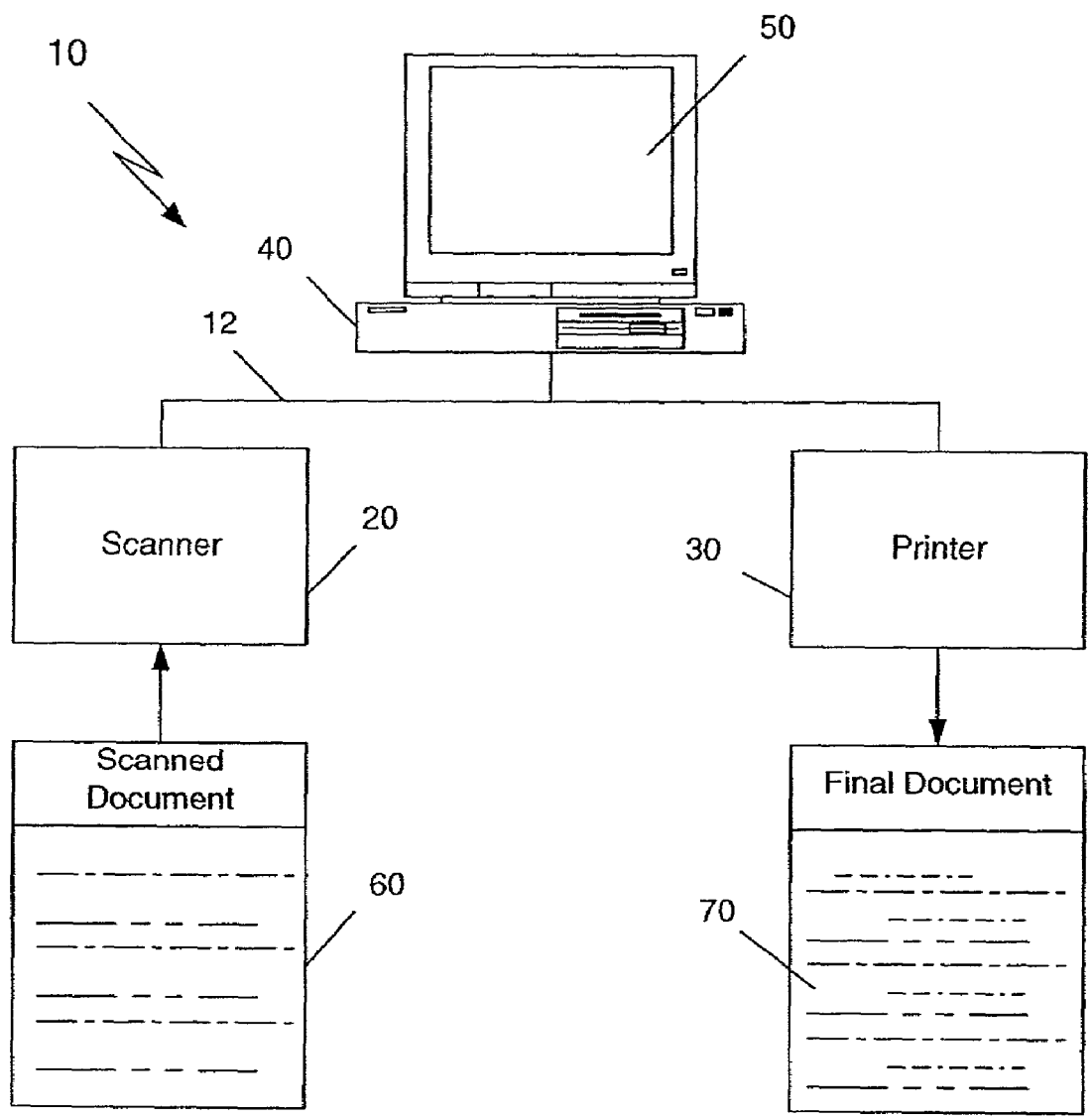
FIG. 1 shows a block diagram of a system for printing form documents.

FIG. 1 shows a block diagram of a system 10 for printing form documents. A computer system 40 is connected by a connection 12, such as a network, to a scanner 20 and a printer 30. In some embodiments, a scanner-printer combination unit (not shown) may be used to serve both purposes of the scanner 20 and printer 30 shown in FIG. 1. The connection 12 may be a hard-wired connection, such as a local area network (LAN), or may be a wireless connection, such as an infrared, radio frequency, satellite, or cellular connection. The computer system 40 includes a display device 50 that displays data.

The system may be used, for example, to use a computer system 40 to add use-data to a hard copy of a form or other document. As used herein, a form or a form document refers to any document to which a user may desire to add user data, and specifically includes without limitation adhesive labels, letterhead and other stationery, user-created documents, and forms such as government forms. User data refers to any information or data that a user desires to add to a form document. The computer system 40 generates an image of a scanned document 60, such as a form. As used herein, the terms form document and scanned document are used interchangeably. The scanned document 60 is scanned into the computer system 40 using the scanner 20. A scanned document image (not shown) is displayed on the display 50 for view by a user. User data is received into the computer system 40 for printing onto the scanned document. The user data may be input using a user input device (not shown), and may be input before or after the scanned document 60 is scanned. In one embodiment, the user data includes data already stored in an electronic format, for example in a memory of the computer system 40. The user data is displayed on the display 50. The displayed user data, in whatever form, is referred to herein as the user data image. The user data image may be, for example, text displayed using a word processing program or an image displayed using a drawing application. The user data image is aligned with the scanned document image so that the user data image may be printed directly to the scanned document in a correct alignment. The scanned document is then inserted into the printer 30, for example into a manual-feed paper tray. The computer system 40 sends the aligned user data image to the printer 30, which prints the user data onto the scanned document 60 to create a final document 70 containing both user data and scanned document data.

Figure 2:
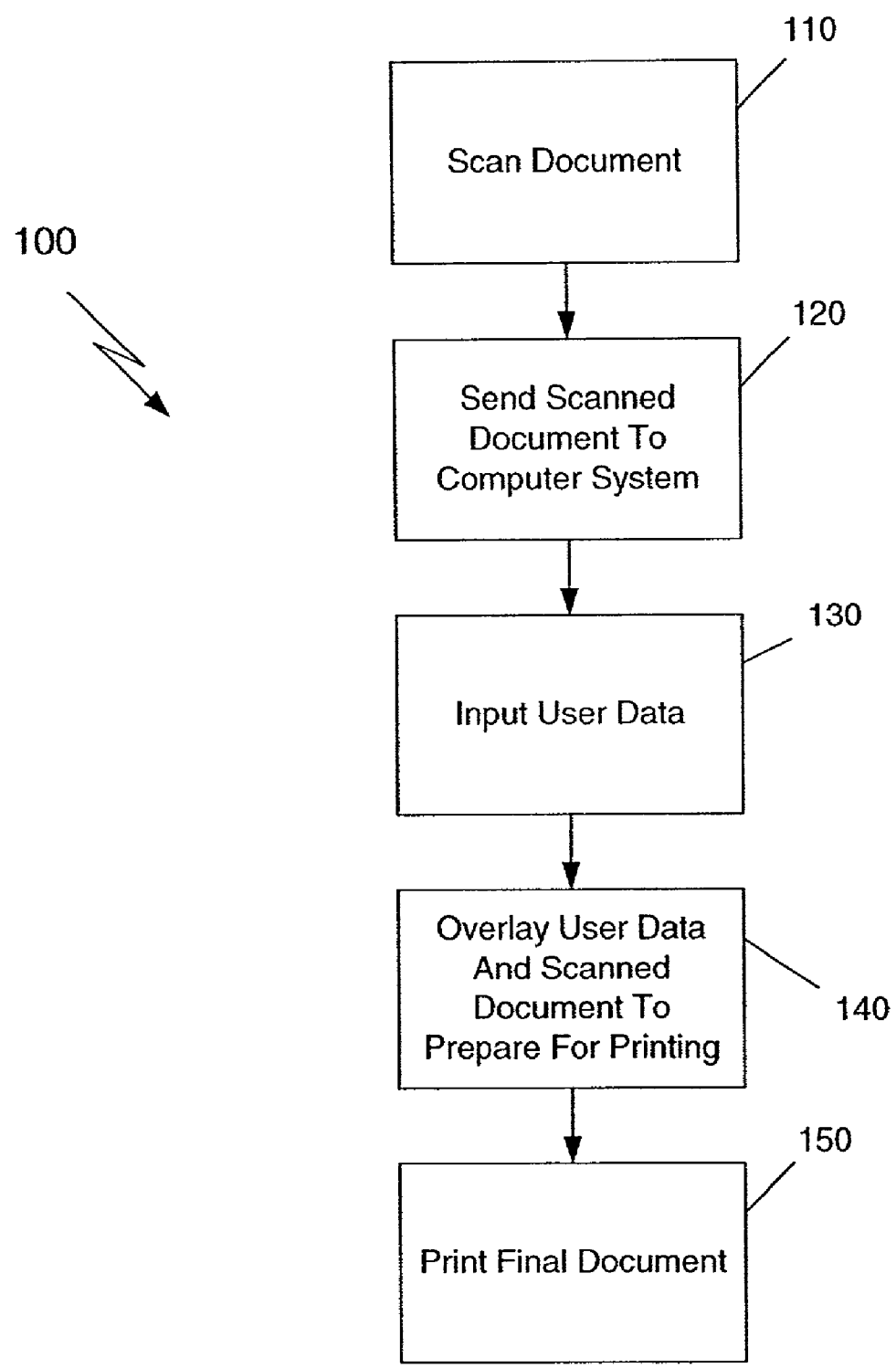
FIG. 2 shows a flow chart of a method for printing form documents using the system shown in FIG. 1.

FIG. 2 shows a flow chart of the method 100 used by the system 10 shown in FIG. 1. The form document 60 is scanned 110 by the scanner 20 and sent 120 to the computer system 40, where it may be displayed on a display device 50. User data is input 130 by a user, either before or after the scanned document 60 is scanned 110. A user data image is displayed on the display device 50 and is overlaid 140 with the scanned document image, such that a user can view both images at the same time with one image on top of the other. The two images are aligned as the user desires. The images may be aligned by moving the user data image relative to the scanned document image. The entire user data image may be moved, or selected portions of it may be moved, for example to align particular user data elements with blanks on the scanned document image. When the images are aligned as the user desires, the final document is printed 150.

Figure 3:
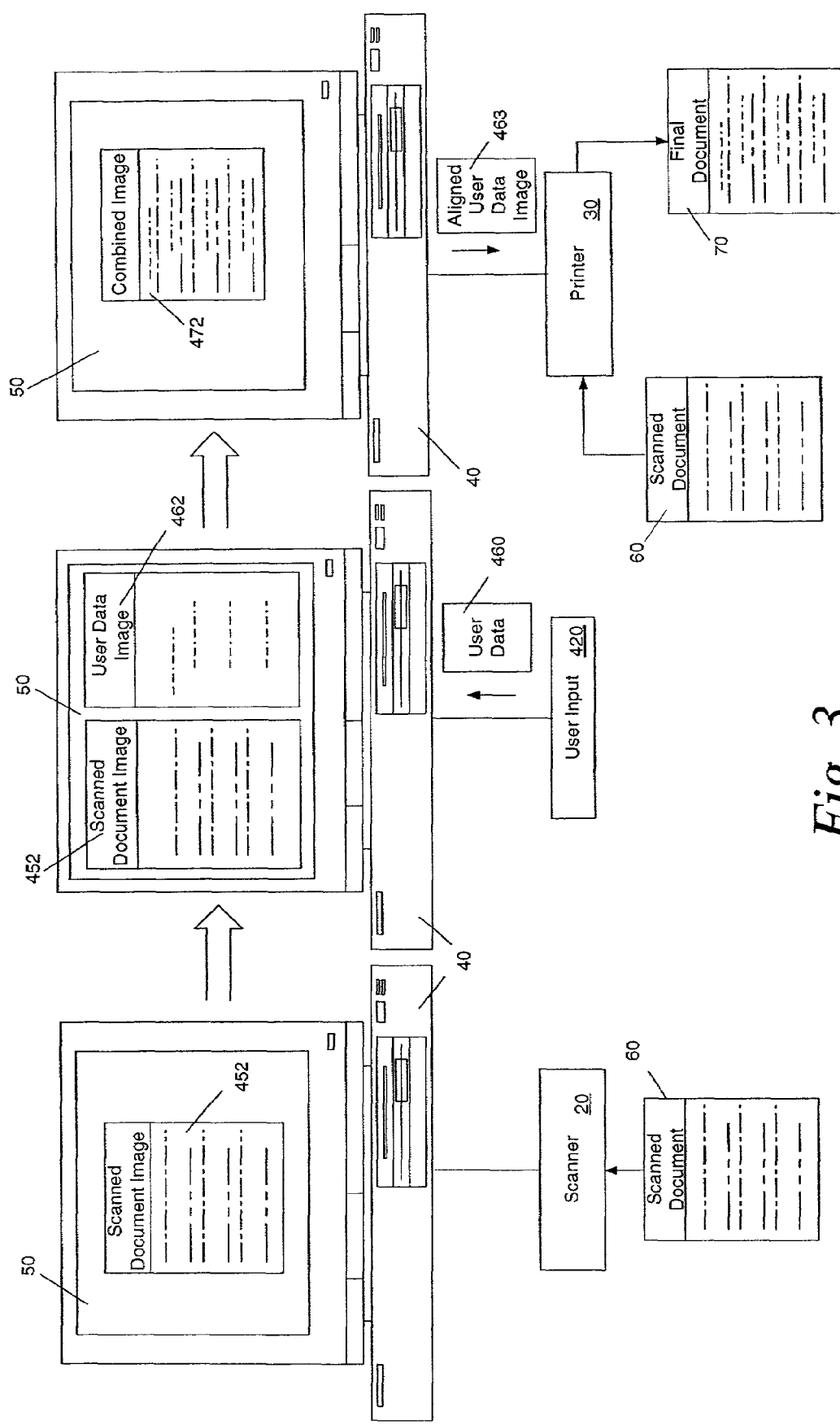
FIG. 3 shows a more detailed block diagram of one embodiment of the system shown in FIG. 1.

FIG. 3 shows a more detailed block diagram of one embodiment of the system 10 of FIG. 1. The embodiment shown in FIG. 3 allows a user to print user data 460 from a computer system 40 directly onto a form document 60 using a printer, such that the user data is aligned with the form 60. The user scans a hard copy of the form document 60 into the computer system 40 using a scanner 20. The form document 60 is displayed on a display device 50 of the computer system 40 as a scanned document image 452. In one embodiment, the scanned image 452 is used only to align user data 460 for printing onto the scanned document 60 and is not printed with the user data image 462. In this embodiment, the scanned image 452 may have a minimal or low resolution to conserve resources. The scanned image 452 may be similar to a "thumbnail" image or a "print preview" image in a word processing program.

In the middle step shown in FIG. 3, user data 460 is input into the computer system 40 using a user input device 420. A user input device 420 includes, for example, a keyboard or keypad or similar input buttons, a mouse or similar pointing device for controlling a cursor, a scanner or camera, a port that receives data, or any other device that receives data controlled by a user. In the case of a form document 60 used as the scanned document 60, the user data 460 may include alphanumeric entries corresponding to blanks on the form 60.

The user data 460 is entered into the computer system 40 into an application, such as a word processing application. The user data 460 is displayed on the display device 50 as a user data image 462. As used herein, a user data image 462 refers to any image that represents the user data 460. In the example of FIG. 3, the user data image 462 and the scanned document image 452 are shown in separate portions, or windows, of the display device 50, and may be formatted in the same or different applications at this point.

The scanned document image 452 and the user data image 462 are then overlaid, or superimposed, to create a combined image 472 as shown on the display device 50 of the right-most portion of FIG. 3. The combined image 472 contains both the scanned document image 452 and the user data image 462. Within the combined image 472, the scanned document image 452 and the user data image 462 may be moved relative to each other to align the two images as desired. In one embodiment, the entire user data image 462 may be moved relative to the scanned document image 452. In another embodiment, specific items of user data 460 within the user data image 462 may be moved relative to the scanned document image 452, for example, to align specific user data 460 with blanks on the form 60. In another embodiment, some items of user data 460 may be linked and moved together, relative to the scanned document image 472. In still another embodiment, each of these alignment methods may be available to the user and/or the computer system 40 to align the user data image 462 with the scanned document image 452 to align the combined image 472.

Once aligned, the user data is printed directly to the hard copy of the scanned document 60. The scanned document 60 may be inserted into the printer's manual feed tray, or other paper source. The aligned user data image 463 is sent to the printer 30 for printing onto the form document 60. The printer 30 prints a final document 70 that includes the user data 460 printed onto the form document 60 according to a desired alignment.

Figure 4:
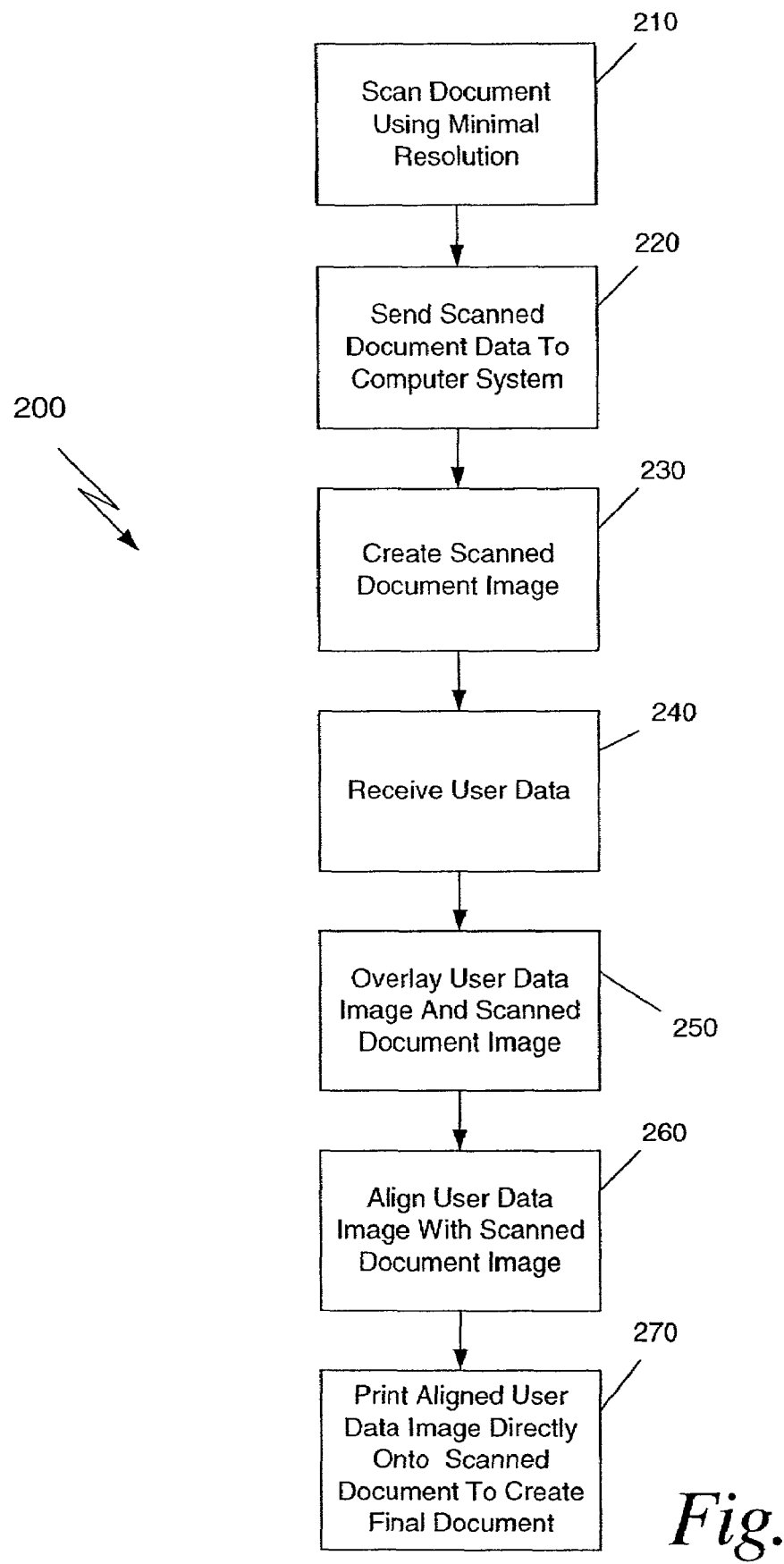
FIG. 4 shows a more detailed flow chart of one method of implementing the system shown in FIG. 3.

FIG. 4 shows a flow chart of the method 200 used by the system shown in FIG. 3. The form document 60 is scanned 210 into the computer system 40 using the scanner 20. In one embodiment, the document 60 is scanned 210 using minimal resolution to conserve memory, processor, and other resources. In this embodiment, minimal resolution is sufficient because the scanned document image 452 is used only to align the user data 460 and is not printed by the system. Data for the scanned document 60 is sent 220 to a computer system 40, such as a desk top computer terminal 40. An image 452 of the scanned document 60 is created 230, and may be displayed. User data 460 is received 240, for example, from a user input device 420, such as a keyboard. The user data 460 is used to create a user data image 462 adapted for display on the display device 50. The user data image 462 and the scanned document image 452 are overlaid 250 such that the display 50 shows both images 452, 462 at the same time, one superimposed on the other. The user data image 462 is aligned 260 with the scanned document image 452, as described herein. The aligned user data image 463 is sent to the printer 30 where it is printed 270 directly onto a hard copy of the scanned document 60.

Figure 5:
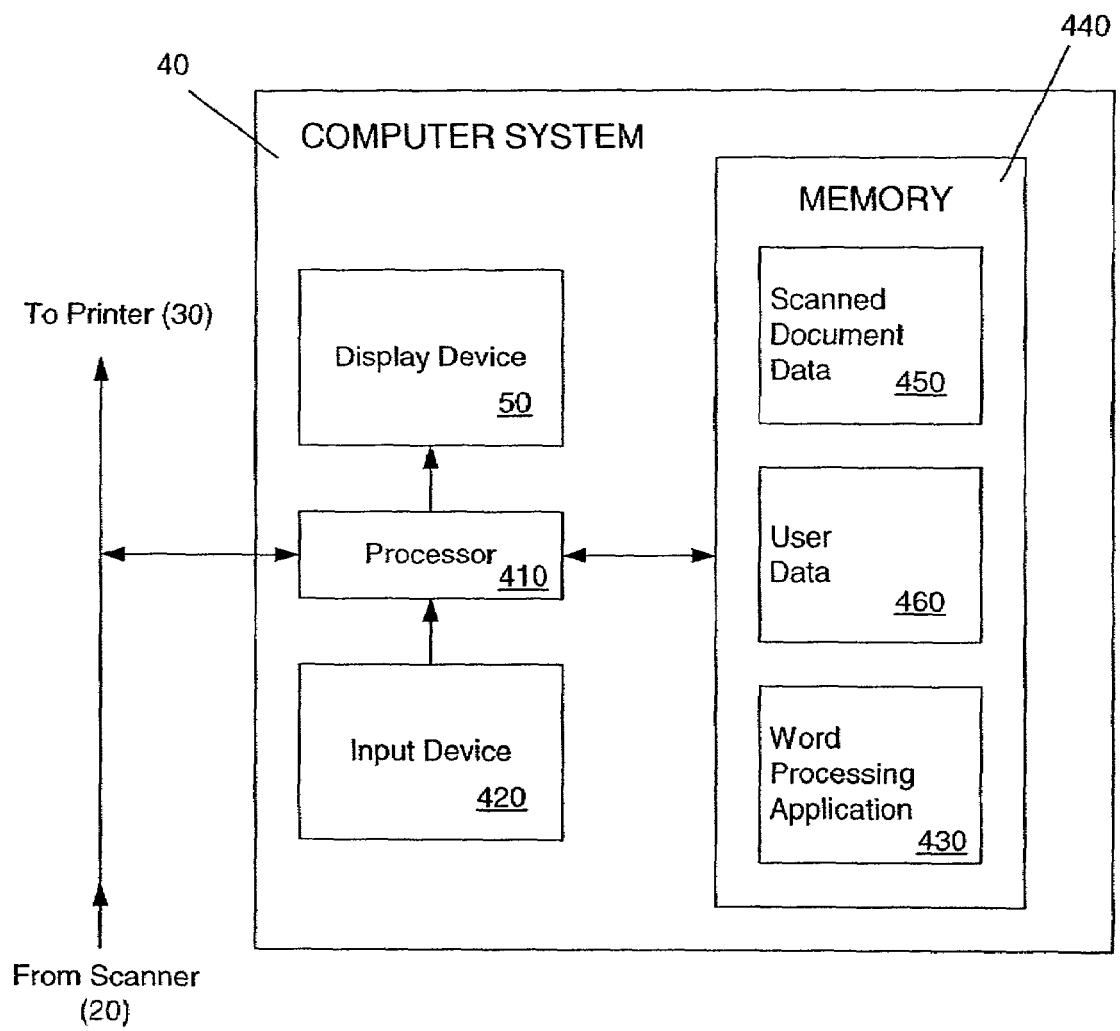
FIG. 5 shows a computer system used by the system for printing form documents.

FIG. 5 shows a block diagram of a computer system 40 having a processor 410 connected to an input device 420 and a display device 50. As used herein, a computer system 40 refers to any processor-based device, and the various computers in the drawings are shown for illustrative purposes only. The processor 410 accesses memory 440 in the computer system 40 that stores scanned document data 450 and user data 460, which are used to create the scanned document image 452 and the user data image 462, respectively. The memory 440 also stores an application 430, such as a word processing application 430, for overlaying 250 and aligning 260 the scanned data image 452 and the user data image 462.

In one embodiment, the application 430 is a word processing application 430 that receives the scanned document data 450 and displays the scanned document image 452 as part of an open word processing file. For example, the scanned document image 452 may be displayed as a background or watermark of a new word processing document. In one embodiment, the user data 460 may be entered and displayed as an image 462 after the scanned document image 452 is displayed, such that the user is able to type or otherwise enter user data 460 on top of the scanned document image 452 background. This allows the user to position user data 460 in a user data image 462 after viewing the scanned document image 452 and knowing where to position user data 460. The scanned document image 452 may be interfaced with a word processing application 430 using software, for example, included as part of device driver software for the scanner 20 and/or printer 30. In one embodiment, device driver software called to generate "print preview," "print setup," or similar word processing features may be used to also display the scanned document image 452. Alternatively, the scanned document image 452 may be displayed in a word processing program 430 as an image that can be moved relative to the user data image 462.

In one embodiment, the application 430 is a stand-alone application that receives the scanned document data 450 and the user data 460 and creates a combined image 472 using various tools that allow the user to align the two images 452, 462. In one embodiment, the application 430 displays the scanned document image 452 as the background and allows the user to position a cursor anywhere on the document and begin typing text at the cursor position, or entering other user data such as graphic or another object. In another embodiment, the application 430 is a conventional word processing, spread sheet, database, or similar application, that interfaces with the scanned document data 450 to produce a background or separate file containing the scanned document image 452. In this embodiment, the user data 460 may be entered as any data is typically entered using the conventional application, for example by typing text in a word processing program or by entering data in cells or fields of a spreadsheet or database program.

Figure 6:
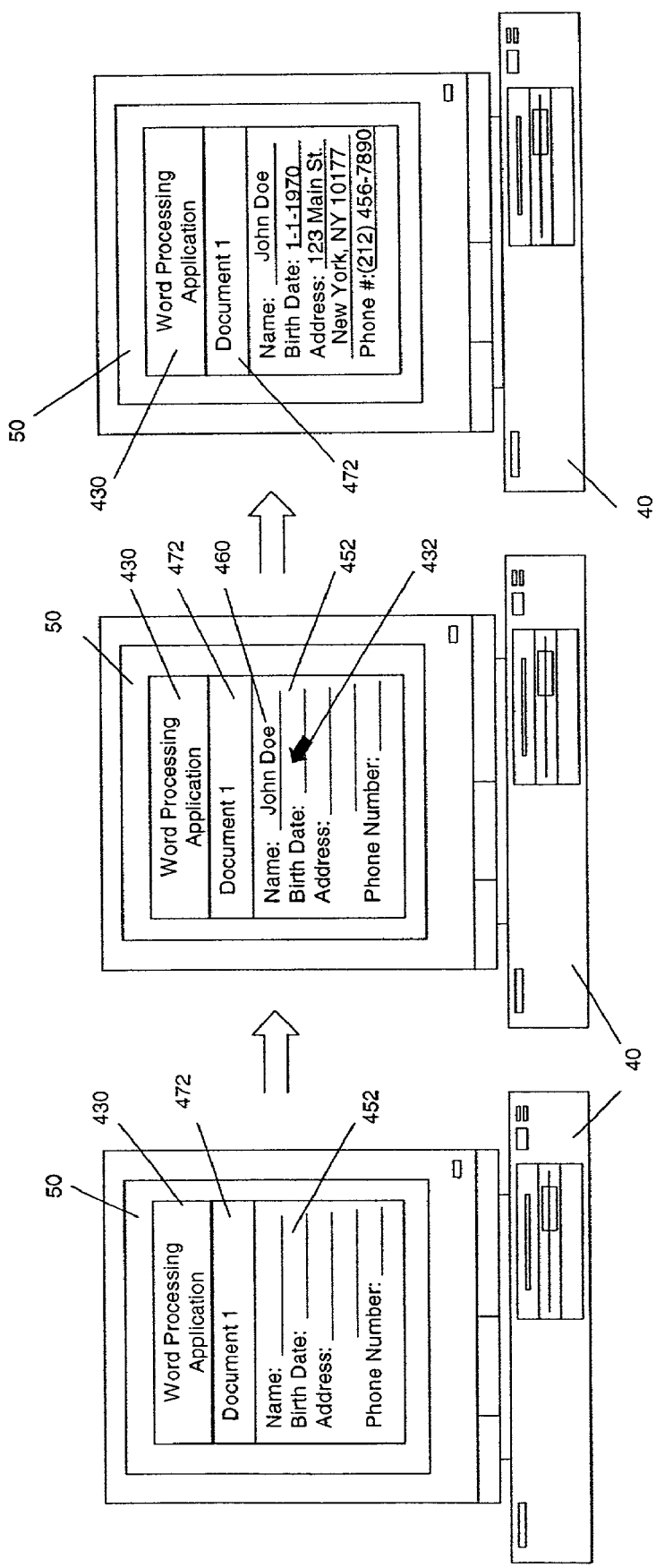
FIG. 6 shows a block diagram of one embodiment of the system in which the scanned document image is used as a background for the combined image.

FIG. 6 shows one embodiment of the system for aligning user data 460 with a form document 60. After the form document 60 is scanned at a low resolution by the scanner, the scanned document image 452 is displayed on a display device 50 of a computer system 40 in a new combined document 472, "Document1," created using a word processing application 430. The scanned document image 452 forms the background of the combined document 472. In the example of FIG. 6, the scanned document 60 includes blanks for a name, birth date, address, and telephone number.

As shown in the middle step of FIG. 6, the user enters user data 460 for these blanks into the combined document 472 by positioning a cursor 432, or similar indicator, using a user input device, such as a mouse device, to a desired place to insert text or other user data 460. In the example of FIG. 6, the user controls the insertion of text by moving an arrow-shaped icon that functions as the cursor 432. The user has entered user data 460 for the name field as John Doe and has positioned the cursor 432 near the birth date blank to begin entering a birth date. In one embodiment, the user may not only position user data 460 by initially selecting a location to enter it, but may also move the data relative to the background scanned document image 452 after the user data 460 is entered.

In the right-most portion of FIG. 6, the user has completed and aligned the combined image 472 in preparation for printing. The user has added user data 460 as follows: John Doe; Jan. 1, 1970; 123 Main St., New York, N.Y. 10177; (212) 456-7890. These user data 460 are aligned with, and displayed on, the display device 50 as a user data image 462 portion of the combined image 472. The aligned user data image 463 is sent to a printer 30 for printing directly onto a hard copy of the scanned document 60.

In another embodiment, the user may merge existing user data 460, for example from a file that displays the user data 460 as a user data image 462, with the scanned document image 452. In still another embodiment, the scanned document image 452 may be used to create a template in a word processing document, into which the user may type or otherwise enter user data 460. The scanned document image 452 may be protected from modification by the user data and, in one embodiment, does not print with the user data 460 so that the aligned user data image 463 may be printed directly onto the hardcopy of the scanned document 60.

Figure 7:
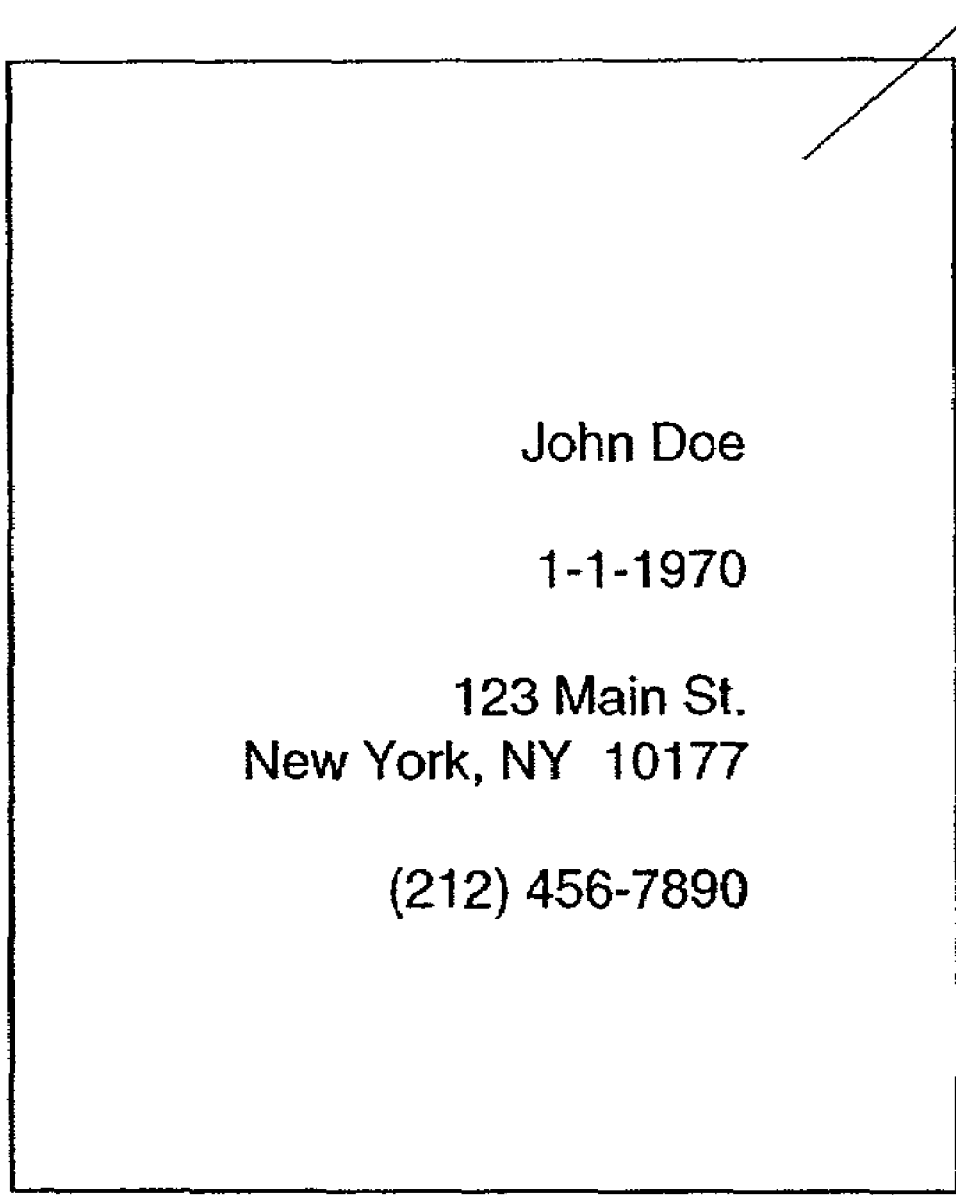
FIG. 7 shows a user data image produced by the example of FIG. 6.

FIG. 7 shows the aligned user data image 463, separate from the background scanned document image 452. If the aligned user data image 463 shown in FIG. 6 were printed on a blank sheet of paper using the printer 30, it would appear as shown in FIG. 7. When the aligned user data image 463 is printed directly onto the scanned document 60, the user data 460 corresponds with desired locations on the scanned document 60, such as blanks in a form or a text portion of a label or letterhead.

Figure 8:
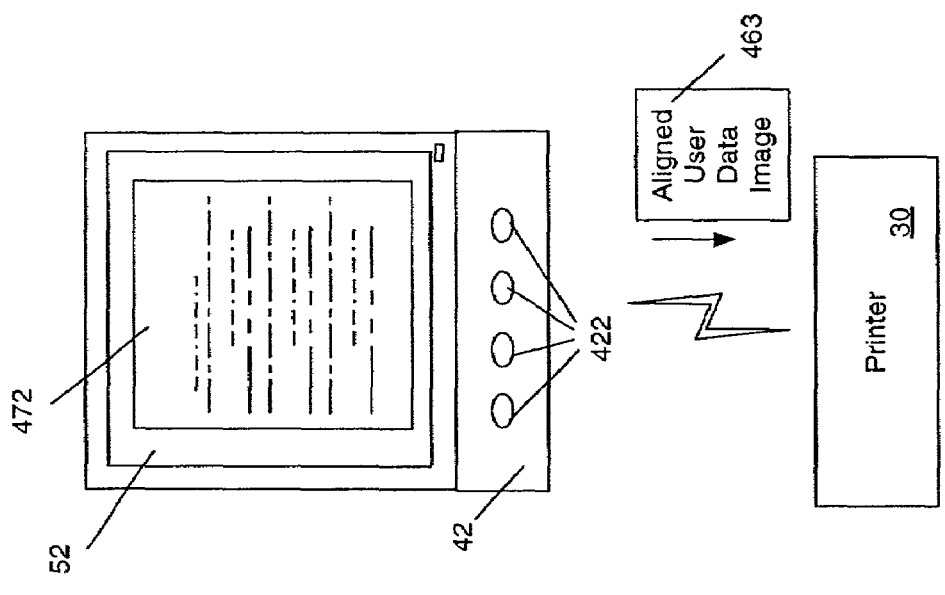
FIG. 8 shows a block diagram of a portable computer system using the method.
Figure 8:
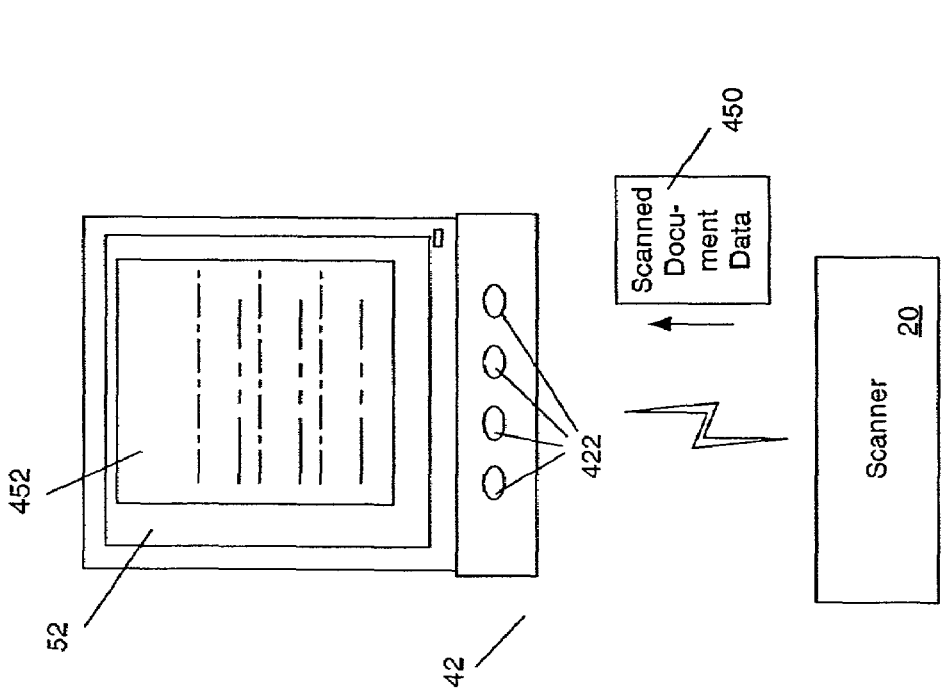

FIG. 8 shows one implementation in which the method and system for printing forms is implemented using a portable computer system 42, such as a palm-sized or laptop computer system. These portable computer systems 42 often have less memory and slower processors than desktop computer systems. These embodiments may use a low resolution scanned document image 452 that requires less resources than a higher resolution image. In the embodiment shown in FIG. 8, the portable computer system receives scanned document data 450 from a scanner 20 via a wireless connection, such as an infrared, radio frequency, cellular, or microwave connection. In this embodiment, both the scanner 20 and the portable computer system 42 have wireless ports (not shown) for connecting to each other.

The portable computer system 452 includes a display 52 that displays the scanned document image 452 using the scanned document data 450 sent from the scanner 20. In the embodiment shown, the display 52 is smaller than conventional desktop monitors and shows only a portion of the scanned document image 452, as indicated. The user then inputs data using user input devices 422, such as the set of buttons 422 shown in FIG. 8. The user input devices 422 may control a cursor used to align the user data 460 onto the scanned document image.

Figure 9:
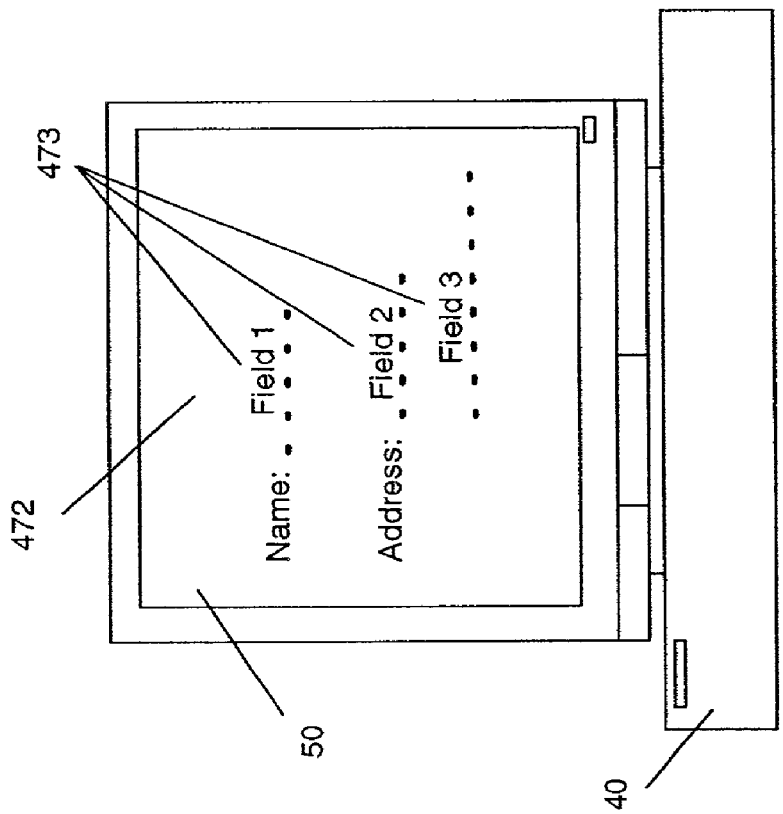
FIG. 9 shows a block diagram of a computer system using user data codes to automatically align user data with the scanned document image.
Figure 9:
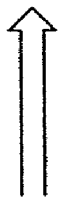
Figure 9:
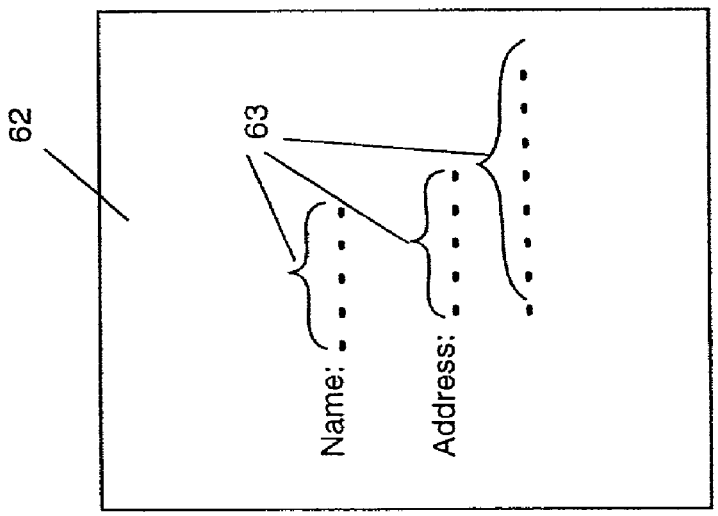

FIG. 9 shows another embodiment in which the scanned document 62 contains user data codes 63 to indicate to the word processing or other application 430 where to enter user data 460. In the example of FIG. 9, the series of four dots on the hard copy of the form document 60 indicates to the application 430 that user data 460 should be entered proximate the codes 63, in this case directly above the codes 63. The document 62 is scanned into the computer system 40, and the scanned document image 452 appears on the display 50 as part of the combined image 472. User data fields 473 appear on the combined image 472, labeled Field 1, Field 2, Field 3 in this example. The user enters data for each of these fields. In one example, the fields 473 create text boxes for the user to enter data at a position on the combined document based on locations of the codes 63. In one embodiment, the user may use a tab key or a similar indicator to automatically move through the combined document 472 from one field 473 to another. Each field should be properly aligned with the desired positions on the form document 62.

In the example of FIG. 9, the text "Name" and "Address" and the codes 63 form the scanned document image 452. The user data 460 entered in the fields 473 form the user data image 462, and the aligned user data image 463 when the user data 460 are aligned with the scanned document image 452 as desired. Together the scanned document image 452 and the user data image 462 form the combined image 472.

Figure 10:
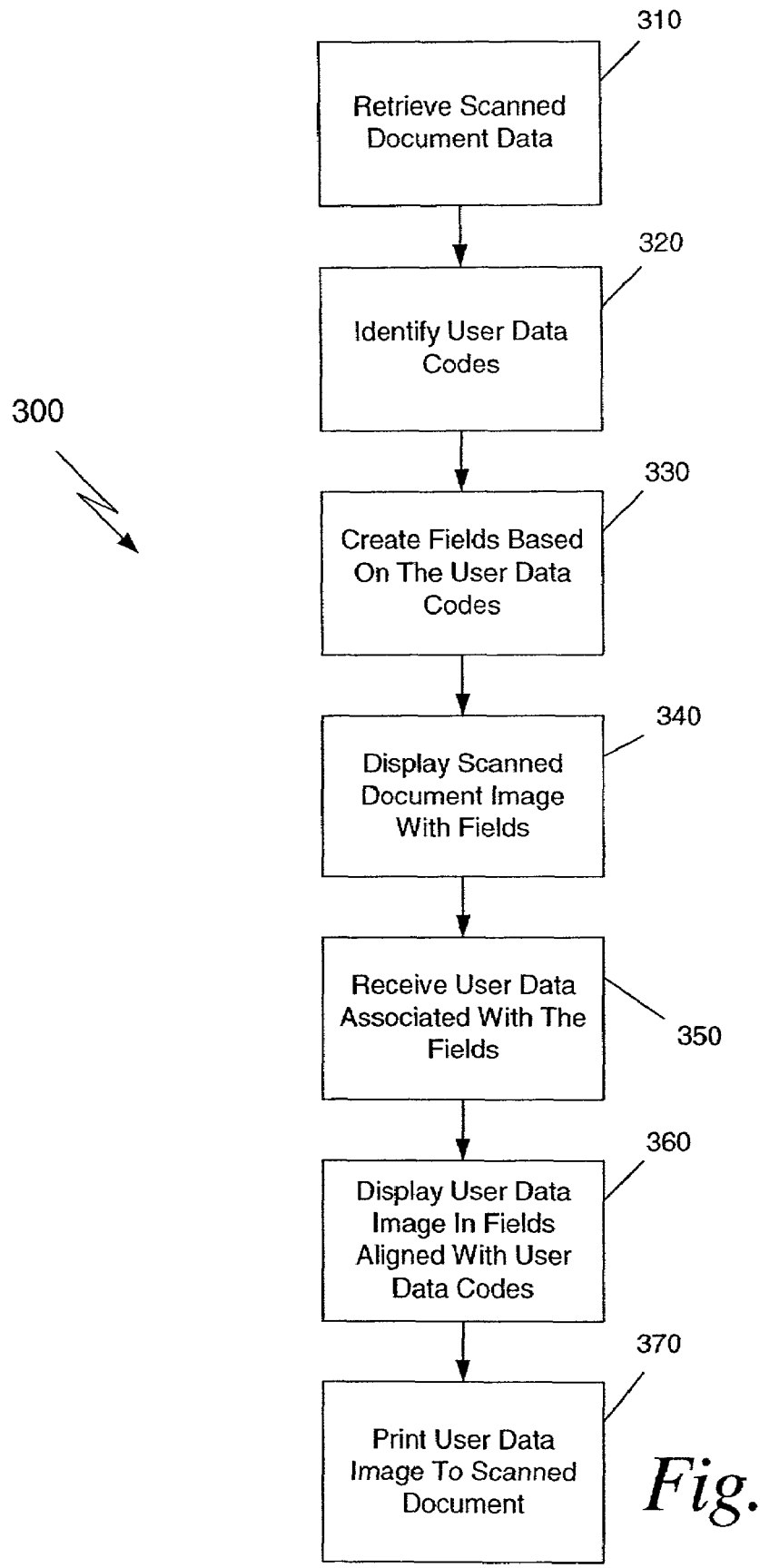
FIG. 10 shows a method used by the computer system to print user data using user data codes.

FIG. 10 shows a flow chart of the method 300 used by the computer system 40 to process the user data codes 63 described in FIG. 9. The method 300 may be performed, for example, by a word processing application 430 stored in memory 440. The computer system 40 receives 310 scanned document data 450 from the scanner 20. The computer system 40 identifies 320 user data codes 63 in the scanned document data 450. For each of the user data codes 63, the computer system 40 creates 330 a field 473 for the entry of user data 460. The fields 473 may be text boxes or other boxes for storing user data 460 to be displayed in relation to the user data codes 63. In one embodiment, different user data codes 63 are used to specify different types of user data 460. For example, one code 63 may indicate that the user data 460 requires a certain sized text box, while another code 63 may indicate that multiple text boxes are required for multiple lines or text, or that an object or graphic will be inserted in the corresponding field 473. The positions of the empty fields 473 align the user data 460 displayed as a user data image 462 with the scanned document image 452. In the example of FIG. 9, the fields 473 are text boxes positioned above the user data codes 63.

The scanned document image 452 created from the scanned document data 450 is displayed 340 on the display device 50, including the empty fields 473. The computer system 40 receives 350 user data 460, for example, from a user input device 420, which user data 460 is associated with the fields 473. In one embodiment, the computer system 40 prompts the user for user data 460 for each of the fields. In another embodiment, the computer system 40 displays a cursor 432 or other indicator in the first field 473 and fills the field 473 with user data 460 as it is entered. Upon receipt of a tab, hard return, or other key stroke or signal, the computer system 40 advances the cursor 432 to the next field 473.

The user data 460 are displayed 360 in the fields 473 and comprise the user data image 462. The user data codes 63 are used to align the user data 460 in the user data image 462 so that the user data image 462 should be aligned with the scanned document image 452 automatically, once the user data 460 is entered. In one embodiment, the computer system 40 allows the user to modify the alignment as desired. Once the images 452, 462 are aligned, the user data image 462 is printed to the scanned document 60 using the printer 30.

Although the present invention has been described with respect to particular embodiments thereof, variations are possible. The present invention may be embodied in specific forms without departing from the essential spirit or attributes thereof. In particular, although the invention is described with respect to its implementation for completing form documents, one skilled in the art will recognize that its application is not so limited. For example, the scanned document 60 may include any typed or other document to which the user wants to add an image or hand notations. In this example, the image or hand notations may be added as user data 460 to the scanned document 60. In addition, although aspects of an implementation consistent with the present invention are described as being stored in memory, one skilled in the art will appreciate that these aspects can also be stored on or read from other types of computer program products or computer-readable media, such as secondary storage devices, including hard disks, floppy disks, or CD-ROM; a carrier wave from the Internet or other network; or other forms of RAM or read-only memory (ROM). It is desired that the embodiments described herein be considered in all respects illustrative and not restrictive and that reference be made to the appended claims and their equivalents for determining the scope of the invention.

What is claimed is:

1. A method of printing user data to a form document comprising:
    receiving scanned document data for a form document;
    creating a scanned document image from the scanned document data;
    displaying the scanned document image on a display;
    receiving user data;
    displaying the user data as part of a user data image, on the display;
    enabling a user to link the user data to another item of user data, such that the linked user data is configured to be moved simultaneously with the another item of user data, relative to the scanned document image;
    automatically aligning the user data with the scanned document image using data codes from the scanned document, wherein different data codes specify different types of user data to be located proximate to the different data codes and, wherein automatically aligning the user data includes,
    identifying the data codes in the scanned document,
    creating fields for the entry of the user data proximate to the locations of the data codes in response to identifying the data codes in the scanned document, and
    inserting the user data specified by the data codes into the fields;
    enabling a user to adjust the alignment of the user data with the scanned document image by linking user data within the user data image into at least one group and aligning the at least one group with the scanned document image; and
    printing the user data onto the form document.

2. The method of claim 1, further comprising displaying a combined image showing the user data image superimposed on the scanned data image.

3. The method of claim 1, wherein the displaying the user data comprises displaying the user data based on the user data codes.

4. The method of claim 1, wherein the receiving scanned document data comprises receiving low resolution data.

5. The method of claim 1, wherein the displaying the scanned document image comprises displaying the scanned document image as a background of a combined image, and wherein the step of displaying the user data comprises displaying the user data on top of the background.

6. A method of printing from a computer to a document, the method comprising:
    scanning a document;
    creating a scanned document image of the document;
    displaying the scanned document image on a display;
    receiving user data;
    creating a user data image from the user data;
    displaying the user data image on the display;
    automatically aligning the user data with the scanned document image using data codes from the scanned document, wherein different data codes specify different types of user data to be located proximate to the different data codes and wherein automatically aligning the user data includes,
    identifying the data codes in the scanned document,
    creating fields for the entry of the user data proximate to the locations of the data codes in response to identifying the data codes in the scanned document, and
    inserting the user data specified by the data codes into the fields
    enabling a user to adjust the alignment of the user data with the scanned document image by linking user data within the user data image into at least one group and aligning the at least one group with the scanned document image, wherein the linked user data in the at least one group is configured to be moved simultaneously, relative to the scanned document image; and
    printing the aligned user data image onto the document to create a final document.

7. The method of claim 6, wherein the scanning comprises scanning the document at a low resolution.

8. The method of claim 6, wherein the displaying the user data image comprises superimposing the user data image onto the scanned document image.

9. The method of claim 6, wherein the displaying the scanned document image comprises displaying the scanned document image as a background of a combined image, and wherein the displaying the user data comprises displaying the user data on top of the background.

10. The method of claim 6, wherein the receiving user data comprises receiving user data from a user input device after displaying the scanned document image.

11. The method of claim 6, further comprising receiving a signal from a user input device related to a position of user data relative to the scanned document image, and wherein the creating the user data image comprises positioning user data at the position.

12. A computer-readable medium having computer executable instructions for performing a method for printing user data to a form document, the method comprising:
    receiving scanned document data for a form document;
    creating a scanned document image from the scanned document data;
    displaying the scanned document image on a display;
    receiving user data;
    displaying the user data as part of a user data image, on the display;
    automatically aligning the user data with the scanned document image using data codes from the scanned document, wherein different data codes specify different types of user data to be located proximate to the different data codes, and wherein automatically aligning the user data includes,
    identifying the data codes in the scanned document,
    creating fields for the entry of the user data proximate to the locations of the data codes in response to identifying the data codes in the scanned document, and
    inserting the user data specified by the data codes into the fields;
    enabling the user to adjust the alignment of the user data image with the scanned document image by linking user data within the user data image into at least one group and aligning one group with the scanned document image, wherein the linked user data in the at least one group is configured to be moved simultaneously, relative to the scanned document image; and
    printing the user data image onto the form document.

13. The computer-readable medium of claim 12, wherein the method further comprises displaying a combined image showing the user data image superimposed on the scanned data image.

14. The computer-readable medium of claim 12, wherein the scanned document data is low resolution data.

* * * * *